United States Patent
Haas et al.

(10) Patent No.: US 8,450,115 B2
(45) Date of Patent: *May 28, 2013

(54) METHOD OF ANALYZING A DISPOSABLE TEST SWIPE

(75) Inventors: Jeffrey Haas, San Ramon, CA (US); Douglas Haas, Lancaster, CA (US)

(73) Assignee: Chem Spectra, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/295,003

(22) Filed: Nov. 11, 2011

(65) Prior Publication Data

US 2012/0094387 A1 Apr. 19, 2012

Related U.S. Application Data

(63) Continuation of application No. 12/354,960, filed on Jan. 16, 2009, now Pat. No. 8,071,385.

(51) Int. Cl.
*G01N 33/00* (2006.01)

(52) U.S. Cl.
USPC ............... 436/50; 436/172; 422/86; 422/87; 422/68.1

(58) Field of Classification Search
CPC ..................................................... G01N 33/00
USPC ....................... 436/50, 172; 422/86, 87, 68.1
See application file for complete search history.

(56) References Cited

U.S. PATENT DOCUMENTS

| 5,296,380 | A | * | 3/1994 | Margalit | 436/106 |
| 5,648,047 | A | * | 7/1997 | Kardish et al. | 422/411 |
| 2005/0101027 | A1 | * | 5/2005 | Haas | 436/109 |

* cited by examiner

*Primary Examiner* — Sam P Siefke
(74) *Attorney, Agent, or Firm* — Tran & Associates

(57) ABSTRACT

A portable chemical analytical apparatus to analyze a test swipe includes a heater to warm the test swipe to a predetermined temperature; a clamp to secure the test swipe to the heater; one or more pumps to dispense one or more chemicals onto the test swipe from a disposable cartridge; a fan to remove chemical vapors rising a predetermined distance from the test swipe; and a camera to capture an image of the test swipe for automated analysis.

5 Claims, 15 Drawing Sheets

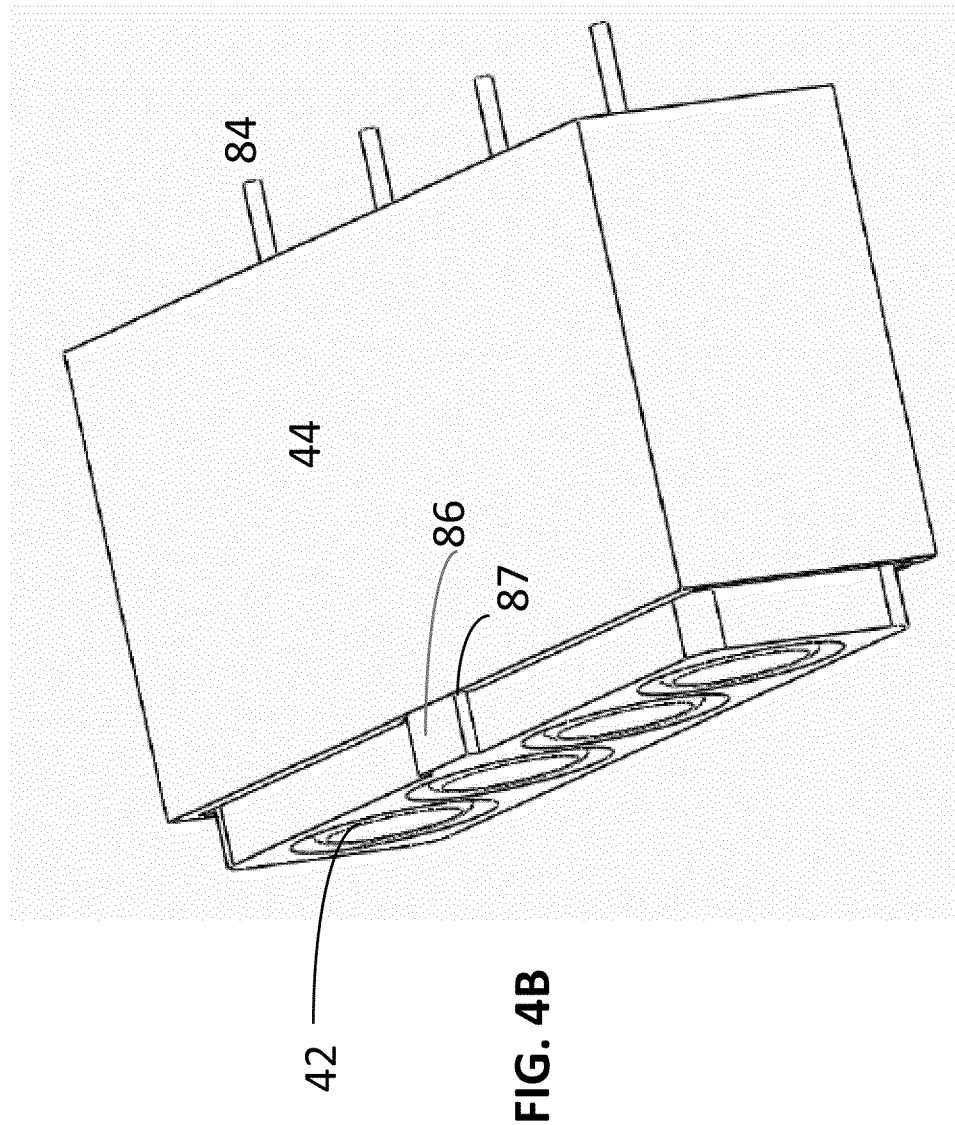

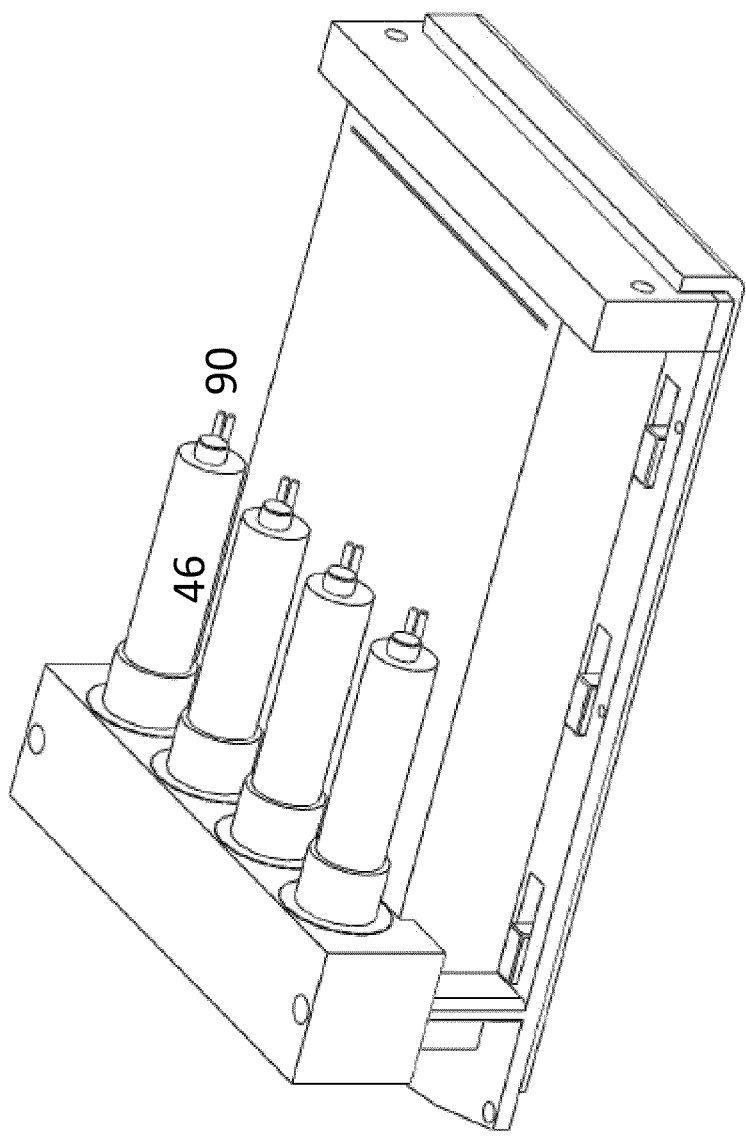

METHOD OF ANALYZING A DISPOSABLE TEST SWIPE

This application is a continuation of U.S. application Ser. No. 12/354,960 filed Jan. 16, 2009 now U.S. Pat. No. 8,071,385, the content of which is incorporated by reference.

BACKGROUND

This invention relates to systems for the detection of explosives and other controlled substances such as drugs or narcotics as well as other chemicals used in clandestine activities.

Recent terror attacks have changed the dynamics of the explosive detection systems across the globe. Terrorists, acting singly or in concert, instill immense fear and apprehension in civilians and governments alike with their technical knowledge about explosives. In parallel, the world has experienced an increase in the transportation of contraband substances such as drugs or narcotics.

With advances in explosives technology, such as the advent of the plastic explosives, which can be disguised as common items, it is becoming increasingly difficult to detect these substances. The problems that must be overcome in the detection of these substances as well as others, include low vapor pressure of the particular vapors escaping from the particular substance, the search time and the throughput of the various systems, the low concentration of vapor or particulate emissions from the particular substance, isolation of the particular substance with a high degree of reliability, and maintaining the integrity of the systems environment.

Various techniques for detecting substances such as explosives and drugs or narcotics have been developed, ranging from explosives/drug sniffing dogs to highly sophisticated vapor detection devices. Machine detection of the aforementioned substances can be accomplished through non-vapor detection or vapor detection. Non-vapor detection methods include x-ray detection, gamma-ray detection, neutron activation detection and nuclear magnetic resonance detection. These methods of detection are more applicable to the detection of the various substances when the substances are concealed and are carried or associated with non-living items such as baggage as these techniques might pose a threat to living items. Vapor detection methods include electron capture detection, gas chromatography detection, mass spectroscopy detection, plasma chromatography detection, bio-sensor detection and laser photo-acoustic detection. These methods of detection are more applicable to the detection of substances that are concealed and associated with living specimens.

Conventional systems tend to be large and immobile. Further, current systems can require users to manually apply toxic chemicals as testing agents. As a result, conventional systems are not mobile and hard to use. Hence, their adoption for field use has been limited.

SUMMARY

In one aspect, a portable handheld chemical analytical apparatus to analyze a test swipe for chemicals such as household, drug, and clandestine, and explosive chemicals is disclosed. The apparatus includes a heater to warm the test swipe to a predetermined temperature; a clamp to secure the test swipe to the heater; one or more pumps to dispense one or more chemicals onto the test swipe; a fan to circulate chemical vapors rising from the test swipe; and a camera to capture an image of the test swipe for analysis.

In another aspect, a method to analyze a swiped sample to identify a chemical composition, includes automatically pumping a series of chemical solution agents into the swiped sample; heating the swiped sample to one or more predetermined temperatures to accelerate the chemical reactions; capturing one or more images of the chemical reaction; sending the images to the a display screen for operator observation; and analyzing the images to identify the chemical composition based on a chemical reaction database.

Advantages of the system may include one or more of the following. The system tests the presence of chemical materials or compounds using a number of factors or parameters singly or in concert. The factors can include heat, volume, time, temperature, and vapor control, among others and sequences these factors over time. The sequences can be in unique intervals. As a result, the system is highly reliable and reduces "false positives" due to its multi-factor, multi-step diagnostic operations.

The system significantly enhances the possibility of accurately and quickly screening personnel, equipment, and materials at security checkpoints, military operations, law enforcement, or other screening scenarios, and for detecting trace of explosive materials. The system allows users to precisely and quickly detect different explosive chemical agents.

The system operates in a real-time fashion. It automatically dispenses a precise volume of chemical solutions over time when requested. The system optionally allows users to manually control the sequence of the pumping process. The system provides users with pump controls for dispensing chemical solutions. Through the built-in heater, the system automatically heats up the swiped sample to predetermined temperatures over specific time parameters using an automatic ramped heating feedback control. The system automatically and continually performs self-check and monitors fluid levels, temperature and time. The system automatically chronologically stores data and arranges according to positive results versus negative results. The system automatically tells the operator to remove the analyzed swipe. The system delivers a unique sequence of precise chemical volumes under time, heat, and vapor parameters. The system has detachable and expendable chemical(s) in cartridge form for ease of replacement. The system uses a high-resolution digital camera for data collection and analysis.

By use of a wired or wireless transceiver, detected information can be easily transmitted to anywhere in the world. By replacing disposable swipes/pads/swabs and disposable chemical test reservoirs, the system can detect a wide range of explosives, clandestine material, drugs, and household products used to manufacture explosives, a range of controlled chemical agents, drugs, and narcotics etc. By allowing the user to swap test materials and running a computerized diagnostics, the user can easily and effectively change the system to meet what is considered to be the threat at that time. By having all components under program control and by arranging for a known input to the system such as a controlled injection of target material, the system can perform self-calibration and self-diagnostic.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not imitative of the present invention, in which:

FIG. 4B shows an exemplary perspective top view of a pump assembly.

FIG. 4C shows an exemplary perspective view of a micro-pump array.

DESCRIPTION

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

Figure 1:
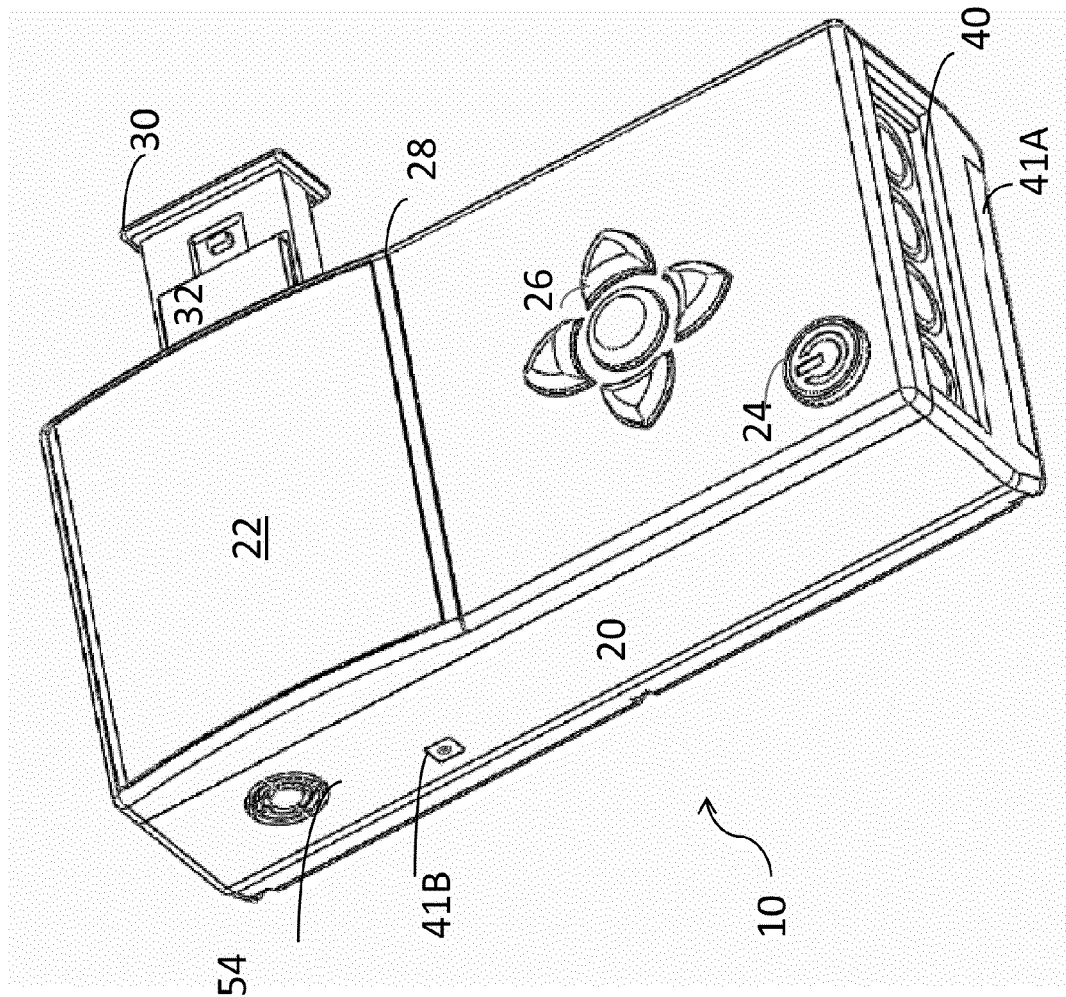
FIG. 1 shows an exemplary portable chemical detection device.

FIG. 1 shows an exemplary portable chemical detection device 10. The device 10 has a housing 20 that supports a display 22 and input devices such as an on-off button 24 and navigation/selection buttons 26. In one embodiment, the system has six buttons. The first button is the On/Off button. This button allows user to turn the unit on or off. The remaining five buttons (Left, Right, Down, Up, and Enter) allows user to interact with a Graphical User Interface (GUI) of the system. The GUI is flexible, efficient and user friendly.

The device 10 also has an input/output port 28 such as a USB port or Firewire port to communicate with a remote computer, and AC power port, among others. In one embodiment, the I/O port 28 is a weather proof PC interface. The PC interface can set up operation parameters and recover analyzed data. In another embodiment, the I/O port 28 can include a flash memory card interface.

The device 10 also includes two ports 30 and 40 to receive user replaceable media and chemical. The device 10 also includes a port 41A to receive user replaceable DC battery cartridge. Port 30 receives a test swipe 32. The port 40 receives a chemical cartridge, which can house one or more chemical containers. An electronic controller 58 (shown in FIGS. 2A AND 2B) receives inputs from the buttons or keys and controls the display 22 and other electronics in the device 10. The system can work with different power sources including battery port 41A port and/or a DC input port 41B such as a car jack or an AC/DC adaptor.

The system of FIG. 1 is preferably a hand-held unit, which can most preferably be operated easily in real time by one operator. Moreover, the operation of such detectors should preferably be simple so that non-technical persons can operate the instrument properly, efficiently, and easily.

Figure 2A:
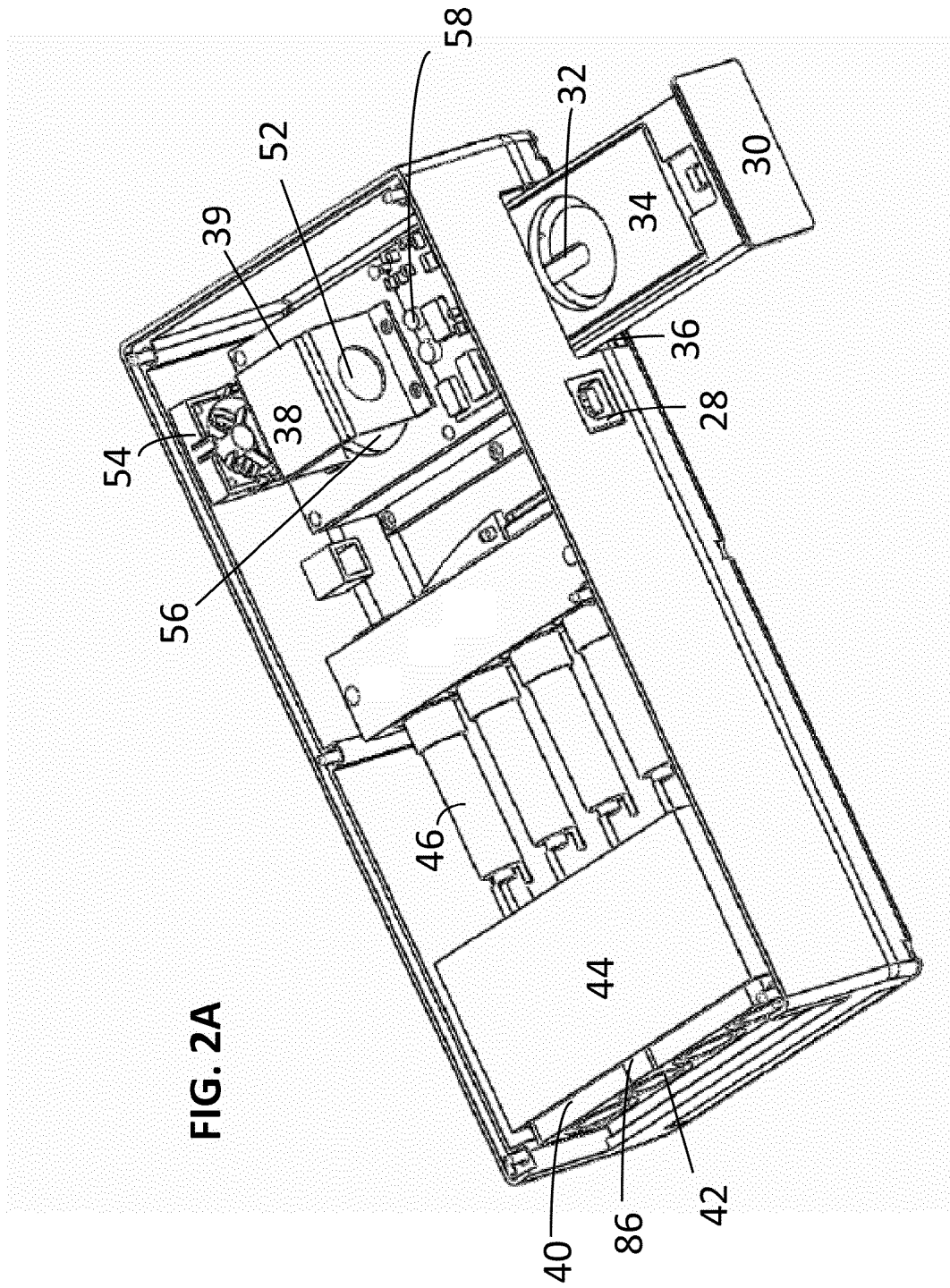
FIGS. 2A and 2B show in more details major components of the device.
Figure 2B:
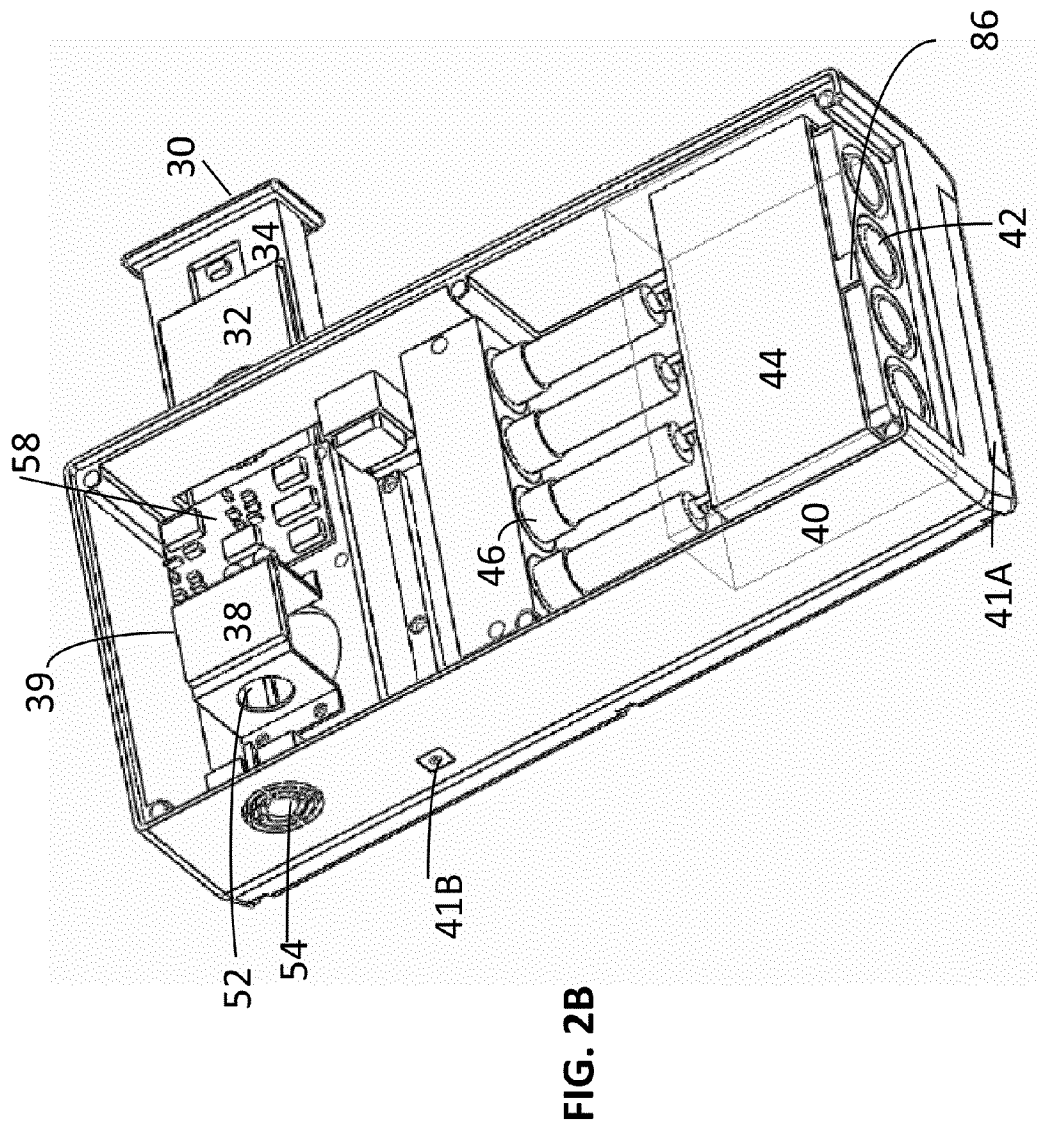

FIGS. 2A and 2B are two perspective top views that show in more details major components of the device 10. In the embodiment of FIG. 2A, a plurality of chemical containers or reservoirs 42 are mounted in a disposable cartridge 44 that is inserted into the unit 10. The reservoirs 42 are punctured via safety needles with a side port and the chemicals are automatically or manually pumped from the reservoirs 42 by one or more micro-pumps 46. The chemicals are delivered through one or more short length and narrow ID delivery tubes connected to the outputs of the micro-pumps 46 to the test swipe 32 during testing.

Figure 5A:
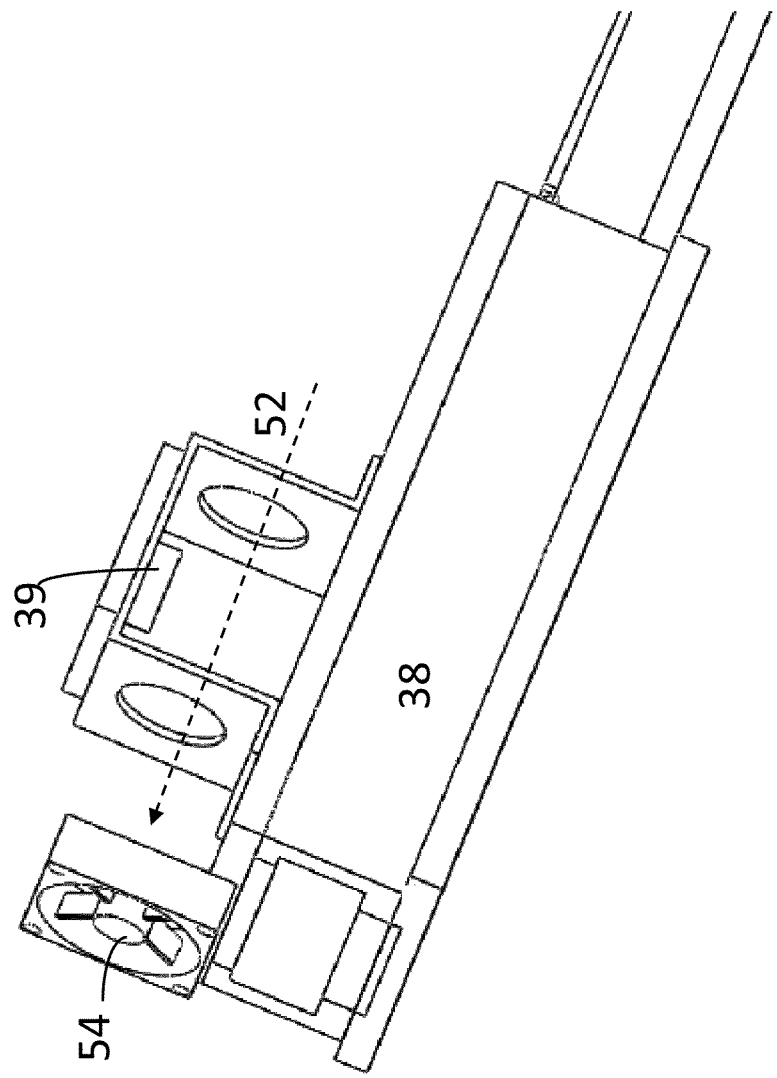
FIG. 5A shows an exemplary perspective view of a camera in a test chamber.

To test a contaminate collection swipe, a user opens the port 30 and places a test swipe 32 into a swipe holder 34. The swipe holder 34 moves along sliding rails 36 when the user closes the port 30 to place the test swipe 32 under a test chamber 38. The test chamber 38 includes a chamber with two openings 52 that face a variable speed fan 54 to draw air across the test swab 32 while under test. The test chamber also includes a heating element 56 connected to a PID loop that can warm up the test swab 32 to multiple predetermined temperature settings during test. The test chamber also contains a camera 39 (FIGS. 2A, 2B, and 5A)

Figure 3:
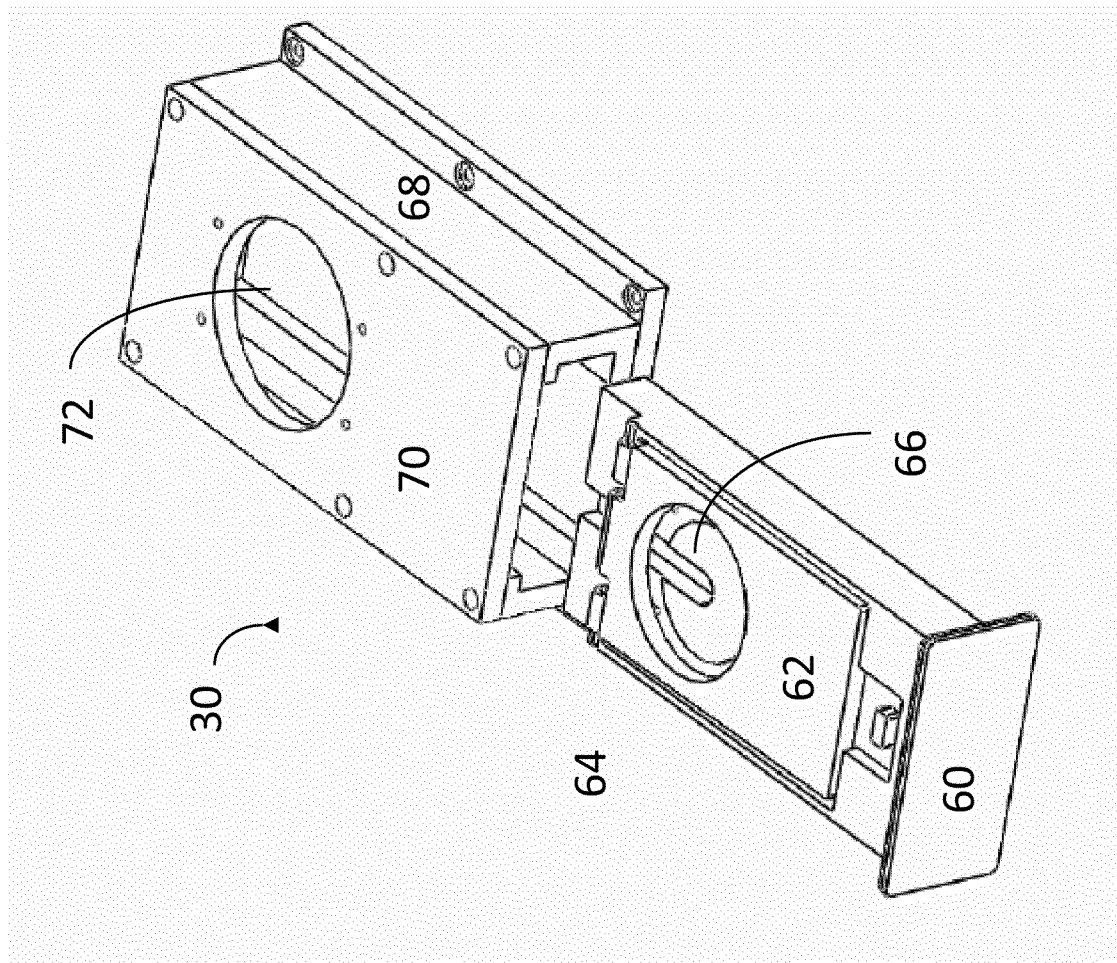
FIG. 3 shows in more details a swipe receiving port.

FIG. 3 shows in more detail port 30 that receives the test swipe 32 in the swipe holder 44 34. The swipe holder 34 includes a door 60 by which a user can press against to open or close the port 30. The swipe holder 34 also includes an open face press-fit clamp 62 that secures the swipe 32 against a heating element 64 under the swipe 32 upon closure. The swipe holder 34 is attached to rails 66 that slide within rails 68 to enable the swipe holder 34 carrying the test swab 32 to move in and out of the device 10. An enclosure for the swipe holder 34 is formed by positioning a lid 70 with an opening 72 between the sliding rails 68. The opening 72 allows movable tubes from the micro-pumps 46 to dispense test chemicals onto the 32. The opening 72 also allows a camera 39 (FIG. 5A) to capture images of the test results for automatic real-time analysis of the test. A white-light source such as an LED is positioned near the camera can be turned on to provide lighting if needed and turned off when not used to conserve power. In one embodiment, the camera output is shown on the display 22 so that the user or operator can visually determine the test result(s) while the automated determination is in progress. The opening 72 also allows a variable speed fan 54 to gently move vapor away from the camera lens to avoid fogging the lens (anti-fogging).

Figure 4A:
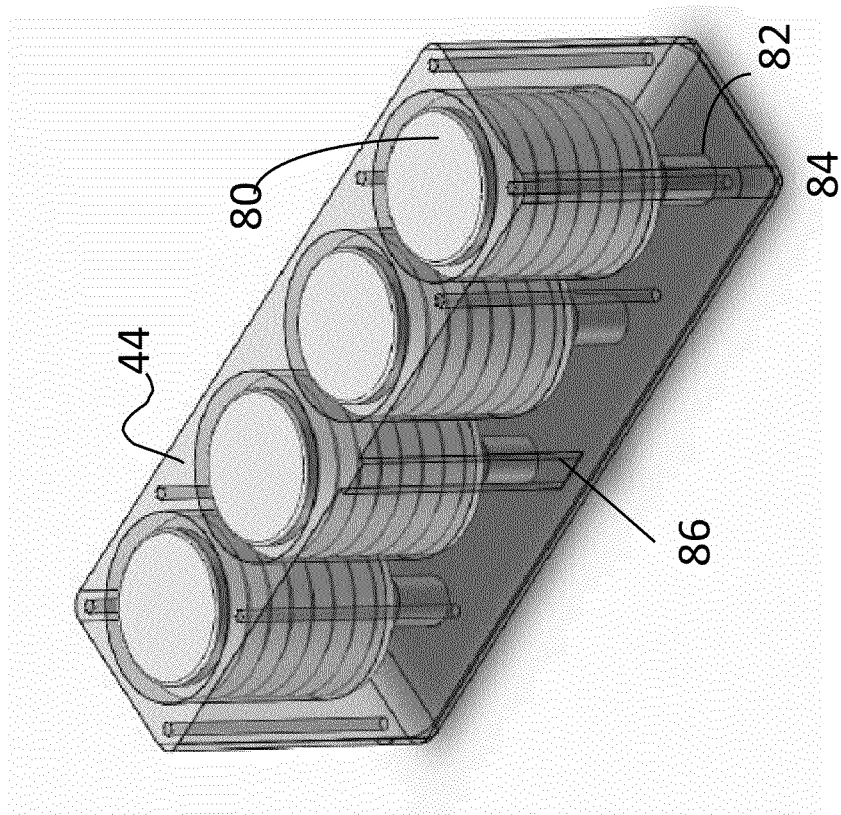
FIG. 4A shows a perspective view of a chemical supply cartridge.

FIG. 4A shows a perspective view of a disposable chemical supply cartridge 44 that can be inserted into the port 40. The disposable cartridge 44 contains one or more reservoirs 80, each having an inlet 82 that can be punctured and is re-sealable so that the chemical in each reservoir 80 can be accessed by a tip or safety needle 84. The disposable cartridge 44 also has a key 86 cooperating with a recess 87 (FIG. 4B) to ensure that the cartridge 44 can only be inserted in a predetermined orientation.

FIG. 4B shows a pump assembly with the cartridge 44. The needles 84 provide chemicals through short length, narrow gauge tubes (not shown) to their respective inputs 90 at the micro-pumps 46.

FIG. 4C shows an exemplary perspective view of a micro-pump array. As shown therein, a plurality of micro-pumps 46 are provided to pump a series of respective chemicals from the array of reservoirs 80. Each micro-pump has an inlet 90 that is connected to the needles that may or may not include safety tips and that are inserted into each reservoir 80 when the user inserts the cartridge 44 into the device 10. Another set of tubes are connected to the outputs of the micro-pumps 46 to deliver the chemicals in precise volume, sequence and timing as controlled by the processing electronic controller 58.

Figure 5B:
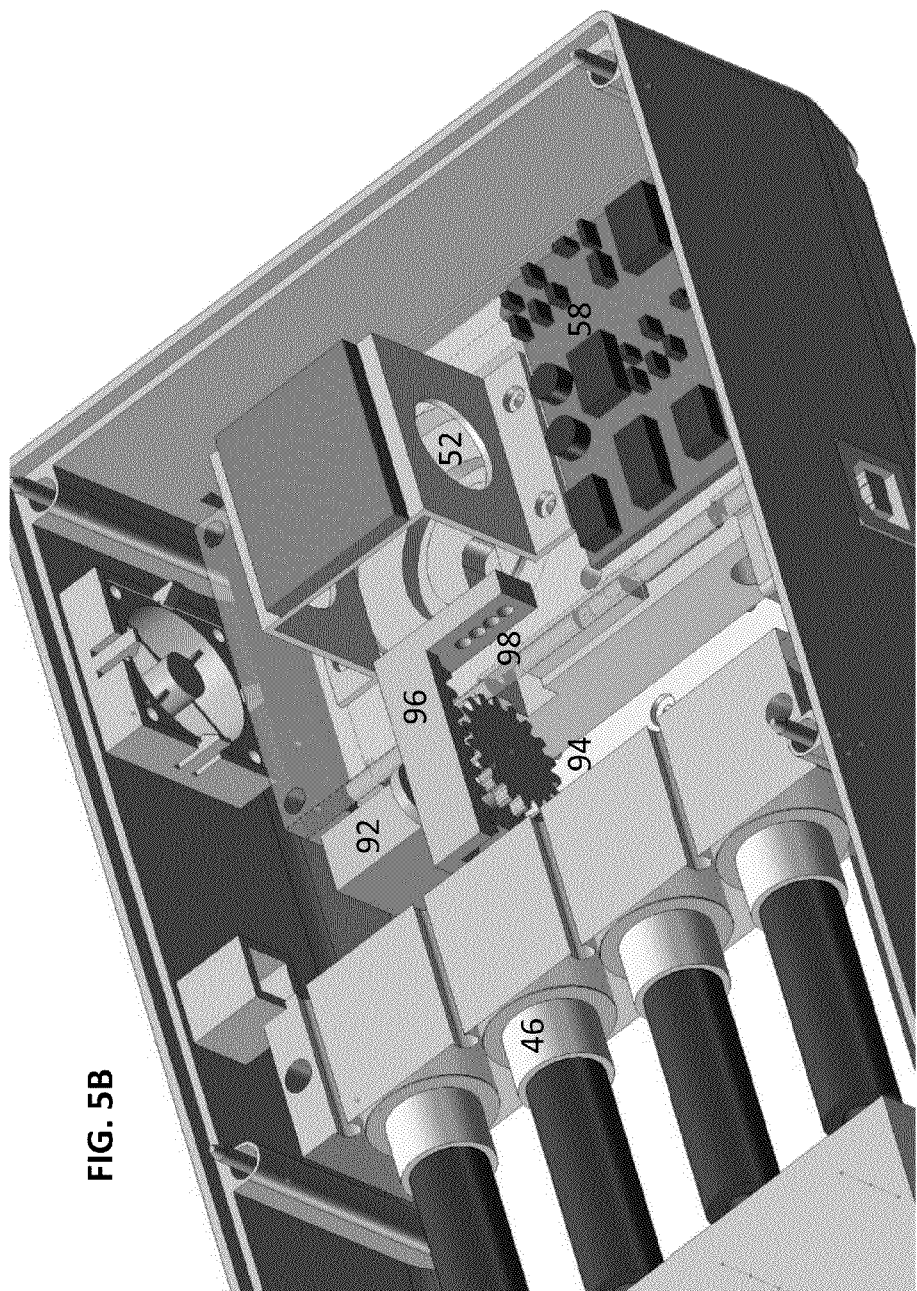
FIG. 5B shows an exemplary perspective view of tubing and camera actuator in the test chamber.

FIGS. 5A and 5B show an exemplary perspective view of a camera 39 in conjunction with the test chamber 38. The chamber 38 includes a motor 92 driving a gear 94. The gear 94 cooperates with a moveable arm 96 that moves test tubing fixture 98 back and forth over the test swab 32 during testing. The test tubing fixture 96 moves very closely to the swipe 32 for chemical deposit onto the swipe when the device 10 is held in any orientation. The arm 96 includes a plurality of openings that receive a plurality of tubes from the output of the micropumps 46. The arm 96 also moves the fixture 98 out of the way for the camera 39 to capture changes on the test swipe 32 during testing. The camera images are then analyzed, and the result can then be displayed on the display 22. In one embodiment, the camera 39 can capture raw images with 65,536 colors. The camera is protected with an anti-fog feature using the adjustable speed fan 54. The image data can be shown continuously throughout the entire process on a flip-up display 22 with high fidelity. In one embodiment, the system provides a software JPEG encoder and decoder for storing and viewing previous results and images. The system also includes white light LEDs (not shown) located within the test chamber 38 that provides even, shadow free, and uniform lighting during camera 39's operation with a programmable white light intensity. The LEDs minimize shadows in the camera viewing area.

The swipe holder 34 moves along rugged sliding rails 66 when the user closes the port 30 to place the test swipe 32 under the test chamber 38. The test chamber 38 includes a chamber with two openings 52 that face the fan 54 to draw air across the test swipe 32 while under test. The test chamber also includes a heating element 56 that can warm up the test swipe 32 to a predetermined temperature during test.

Figure 6:
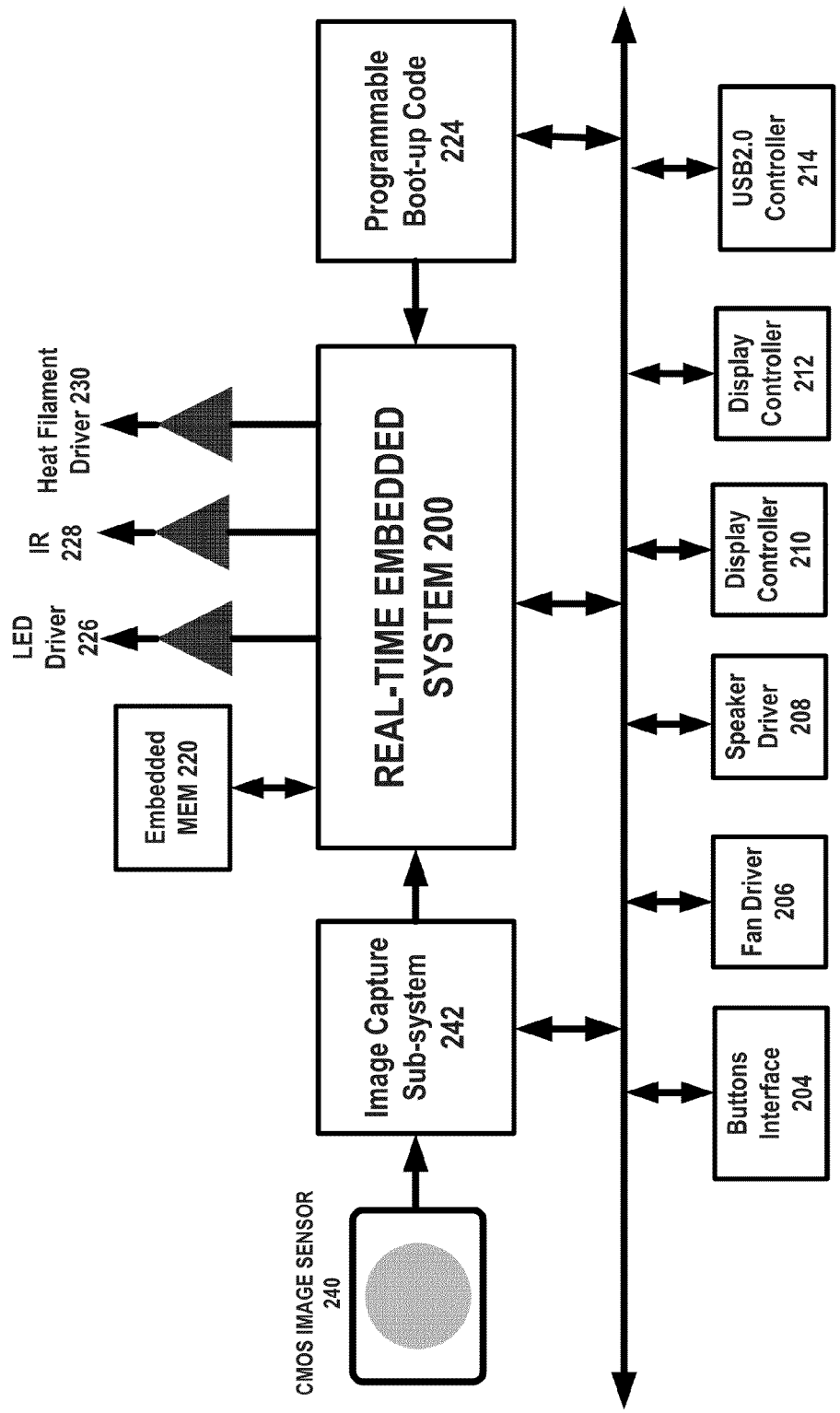
FIG. 6 shows an exemplary block diagram of processing electronics for the system of FIG. 1.
Figure 7A:
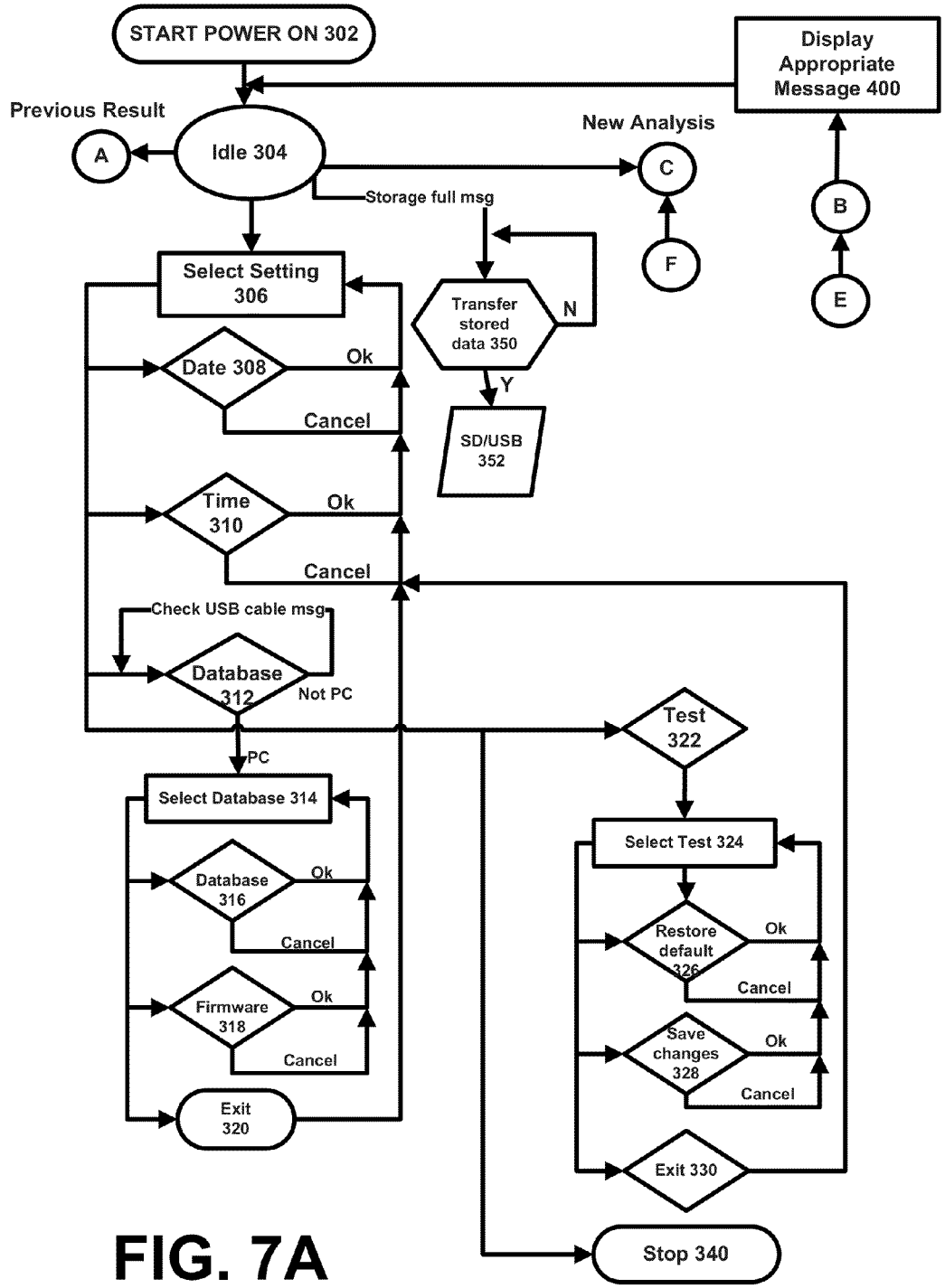
FIGS. 7A-7D show an exemplary operational flow chart executed by the system of FIG. 1.
Figure 7B:
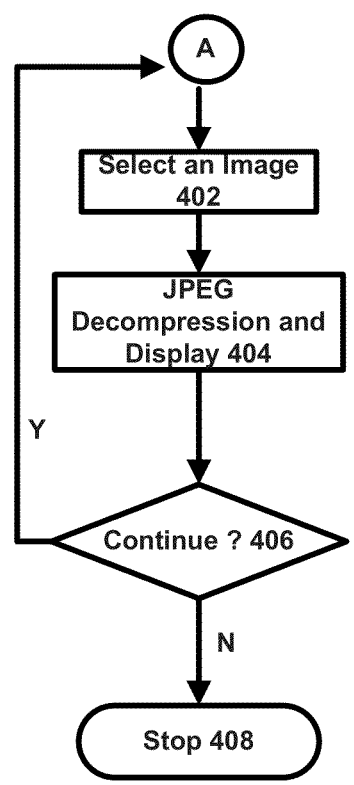
Figure 7C:
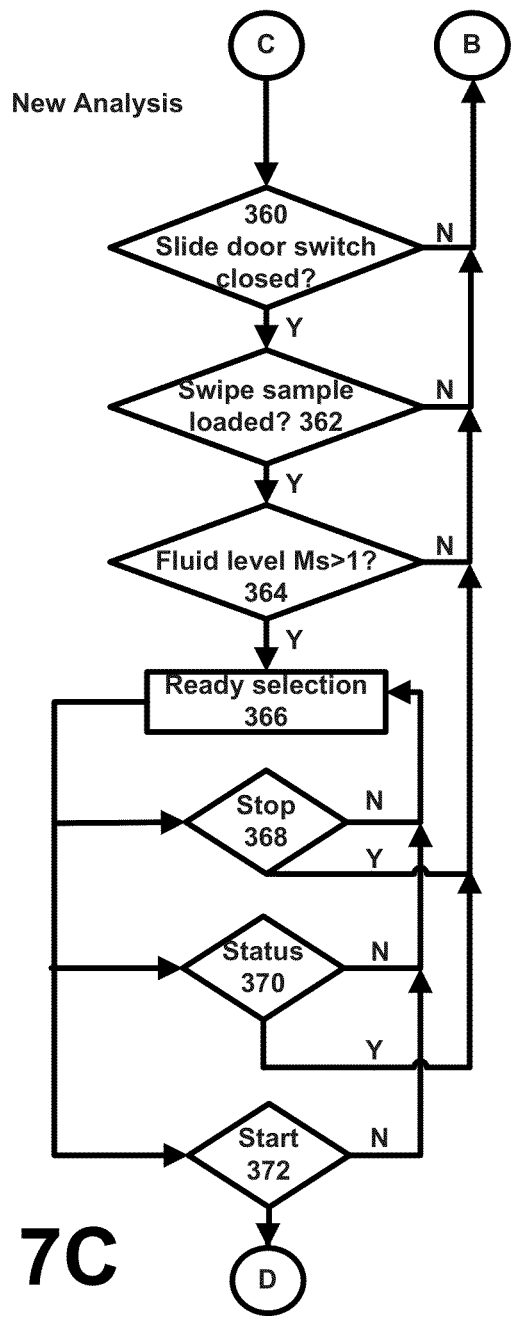
Figure 7D:
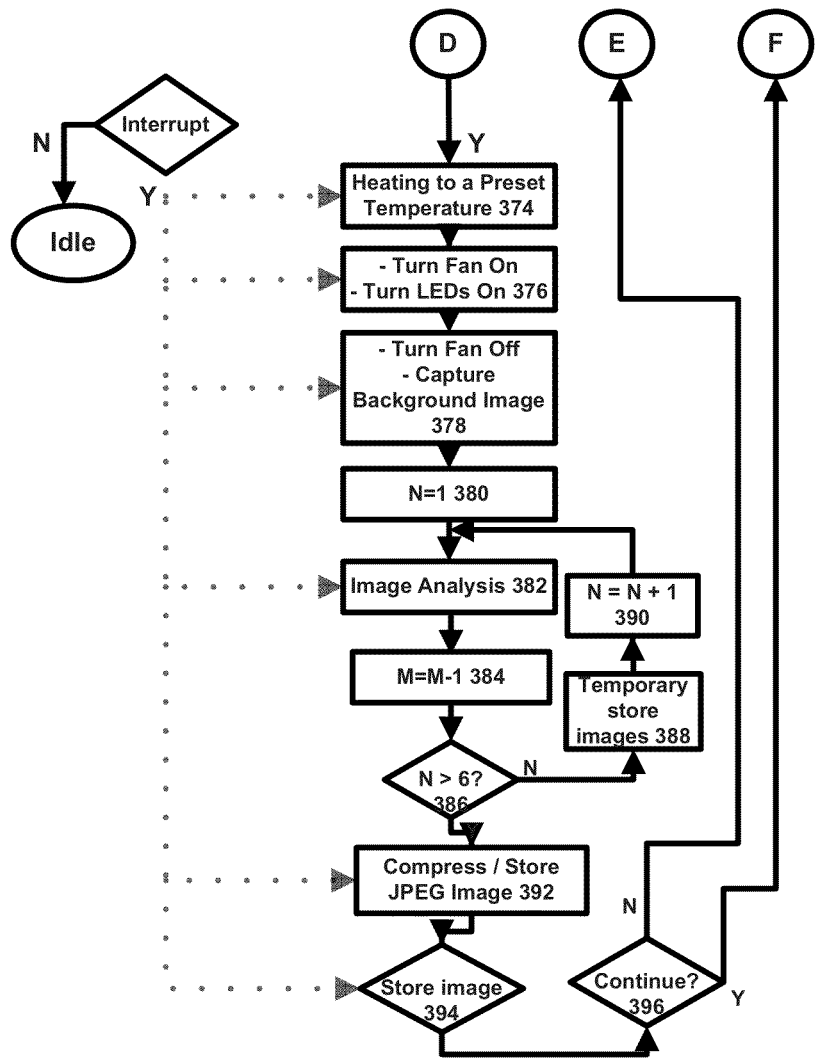

FIG. 6 shows an exemplary block diagram of processing electronics for the system of FIG. 1. A processor 200 controls all tasks done by the system. The processor 200 communicates over a bus 202 to various devices, including buttons interface 204, fan driver 206, speaker driver 208, display controller 210, micro-pump driver 212, and USB controller 214. The processor 200 also communicates with embedded memory 220 and a programmable ROM 224 that contains boot code as well as application code. The processor 200 also drives buffers 226, 228 and 230 which controls the LED, infrared sensor that informs the operator if a swipe has been loaded into the test chamber 38, and heat filament, respectively. The infrared sensor is positioned under the swipe and acts as a proximity sensor to detect the presence or absence of a swipe by the amount of light reflected back. The processor 200 or controller actuates the motor to drive a solution delivery manifold to the center of the swipe and in close proximity to the swipe to dispense the solution without dripping, regardless orientation. The controller can monitor fluid levels within each reservoir contained in the disposable cartridge. This is done by decrementing available volume each time the pump is actuated and when the count reaches a low threshold, the controller can indicate that the reservoir is out of chemical.

The system is powered by a 12-volt DC source, which can be generated from an AC/DC converter, a car outlet or from eight 1.5-volt batteries in series. The highest prioritized energy source is from an AC/DC converter followed by the one from a car outlet, then the energy from batteries. The 12-volt DC power source will supply current to the heater and the pump. It is also connected to the low drop voltage regulator to generate different voltage levels such as 5 V, 2.8 V and 3.3 V, which are necessary for the processor and for other peripherals as well.

In one embodiment as a Portable Explosive Trace Detector (PETD), the system of FIG. 6 significantly enhances the detection of the explosive materials as well as speeding up the screening and detecting procedures at security checkpoints. First, the PETD automatically pumps a series of chemical solution agents into the swiped sample and heats up to specific temperature to accelerate the chemical reactions. Second, an internal CMOS camera captures the chemical reaction images at its highest resolution, raw data for better image analysis. Third it then sends these raw images data to the LCD (Liquid Crystal Display) screen for the purpose of observation. Moreover, the JPEG codec will be develop for storing and replaying image functions. The LCD screen provides a high quality image for human viewing. The LCD can analyze the image to identify explosive materials based on the provided chemical reaction database. Last but not least, the PC interfaces can be used to update software and firmware as well as to backup the data.

In one implementation, to start the analysis process, the system turns the micro-pump(s) N (i.e., N=1, 2, 3 . . . or a combination thereof) to disperse the chemical solution into the Swiped Sample. The pumping rate is set to 2 Hz. After dispersing chemical solution, the system starts heating the sample to excite the chemical reactions under controlled vapor, time, temperature, and chemical volume conditions specific to a particular analyte or group of analytes. A current of about one ampere is applied to heat up the heating filament. During the heating process, the fluctuation of the temperature is controlled by a feedback circuit with a thermistor.

When the temperature of the sample swipe reaches a predefined value, the system turns the heater off, the white light LED on and the fan on. The speed of the fan is adjustable using pulse width modulation control in one embodiment.

Before commanding the camera's CMOS image sensor to capture an image, the system waits for the chemical reaction to complete for around 1 ms. The captured image is then displayed on the LCD.

The system creates a result image by subtracting the captured image from the background one. Then the result image is compared with the color patterns in the lookup table stored in the system. If the results image matches some color pattern, the result probability will be displayed and an optional audible alarm is given or not. Otherwise, an appropriate message is displayed on the LCD.

During the process of writing to the memory, (e.g., saving results or updating database), the system is able to detect the memory capacity and give the user a warning of full memory. In such a case, the user needs to clear the memory by deleting certain files before commanding the system to continue its work.

In one embodiment, the system executes a prime pump procedure to clear up air and chemical bubbles in the tubes of minimized length and diameter once the system has been idled for more than 12 hours. If the system has not been used for the past 12 hours then the system prompts the user to place an empty swipe sample into a clamp holder. Once a swipe sample is secured on the clamp holder, the system prompts user to do the prime pump procedure by pumping chemical solutions onto swipe sample. During the prime pumps, the camera captures the image from the swipe and displays it on the LCD screen. During the prime pumps, no heat is applied to the swipe.

In one embodiment, in the main menu, user can see the date, the time and current status of the system. The system can generate a warning alarm once battery, chemical level and memory reach their minimal levels. The menu also contains three (3) software programmable buttons, namely New Analysis, Previous Results, and Settings. User can interact with these soft buttons by using the five hard buttons. The New Analysis option is highlighted as default. The usage of these soft buttons is as follows:

New Analysis: allows user to perform a new test.

Previous Results: allows user to trace back the data tested in the past.

Settings: allows user to set parameters such as date, time, to test the system reliability, or to connect to PC for firmware and/or database update.

The user can see the images taken by the camera. The system status is also displayed. In addition, three (3) soft buttons (Start, Stop, and Status) are provided. The Start option is highlighted as default.

FIGS. 7A-7D (collectively FIG. 7) show an exemplary operational flow chart executed by the system of FIG. 1. When the system is turned on by pressing the Start Power On button, it will stay in IDLE state 304. In this state, the system waits for user commands. By default, both the camera lighting LED and the fan are turned off. The system sends an appropriate message alarm to operator once chemical, battery, and memory reach their minimal level. User may command the system to perform a new test by selecting New Analysis, to view previous results and images by selecting Previous Results, or to update the firmware and/or database.

When the option of performing a new test is selected, the system checks whether the Slide Door Switch closed or not (360). If the door is not closed, it will display a warning message (400) and return to IDLE state 304. Otherwise, it looks for a loaded Swiped Sample using the infrared sensor (362). The presence of the sample allows the system to move to the next state, where it checks for the fluid levels of the three reservoirs to ensure that the fluids are enough for the entire test process (364). The amount of fluid is determined by the number of dispersing (i.e., a full bottle is enough for a predetermined number of dispersals and the number is decremented during each dispersing).

Before continuing, the system checks the temperature of the filament if it is equal to 35° C. in one embodiment. Otherwise, it will have to heat the filament until the temperature of the filament reaches 35° C. (374). At this temperature, the user is allowed to choose different options. If the user presses the Stop button (368), the system will stop the work and return to the IDLE state. If the user chooses the Status button (370), the system will temporarily display its current task to turn the system status on/off. After that it returns and continues the previous work. When the user presses Start button (372), the system turns the Fan on to blow the fog or vapor away from the camera, turns the LEDs on, turns the fan 39 to a low speed and takes a background image using the camera (378). Then, the system will select a particular micro-pump N=1 or a series of micro-pumps (N=1, 2, 3 . . . or a combination thereof) and start analyzing the sample based on the image analysis process (380-386). Once the New Analysis operation is in process, it takes a number of different tests (in one embodiment seven tests) non-stop and summarizes the test results after the last test has completed. The image results are saved automatically as a group by a time date stamp and can be further sorted by positive or negative results for ease of viewing recall (392-394). Different audible sounds can be played at the end of each test to catch the operators attention. The image result is obtained by subtracting the current image from its initial background image. After finishing this analysis, the system asks user if he/she wants to review the test summary or else return to the main menu.

When the option of viewing previous results is selected, the user can select his/her desired filename and presses Display button to command the system to decompress and display the image and/or other necessary information (402-408).

When the option of updating date, time, database and/or firmware is selected (306), the system shows a menu to allow the user to choose different options such as update date, time, or upgrade the firmware, or test the reliability of the system. For example, when the user presses the date button (308), the system allows the user to change the date via the buttons of the system. After the date is confirmed to be changed, the system will store the change in its memory and return to the previous menu to allow the user to choose other options. The change of the time functions in the same manner as the change of the date (310).

In case the user wants to update the database by pressing Database button (316), the system communicates with the PC in order to set up a channel for data transfer (312). Upon a successful connection the user can update database and/or firmware. After the firmware or database is updated, the user presses the Ok button to return to the main menu. When the system connects to the PC unsuccessfully, it warns the user to check the connection (316).

When the user wants to test the reliability of the system, the user can press the Test button (322). As soon as this button is pressed, the user can test different system parameters. He/she can save the changed parameter or restore default parameter. When the user presses Exit button, system returns to the main menu.

By having all components under program control and by arranging for a known input to the system such as a controlled injection of target material, the system can perform self-calibration and self-diagnostic. The function of this program is to calibrate the entire system and determine and store the required time, and temperature parameter, among others. If these parameters are not within specified limits for any reason, the program can alert the user. Guided by a service program the user response can range from immediate shutdown to scheduling service at a later date, to simply noting the circumstances.

Figure 8:
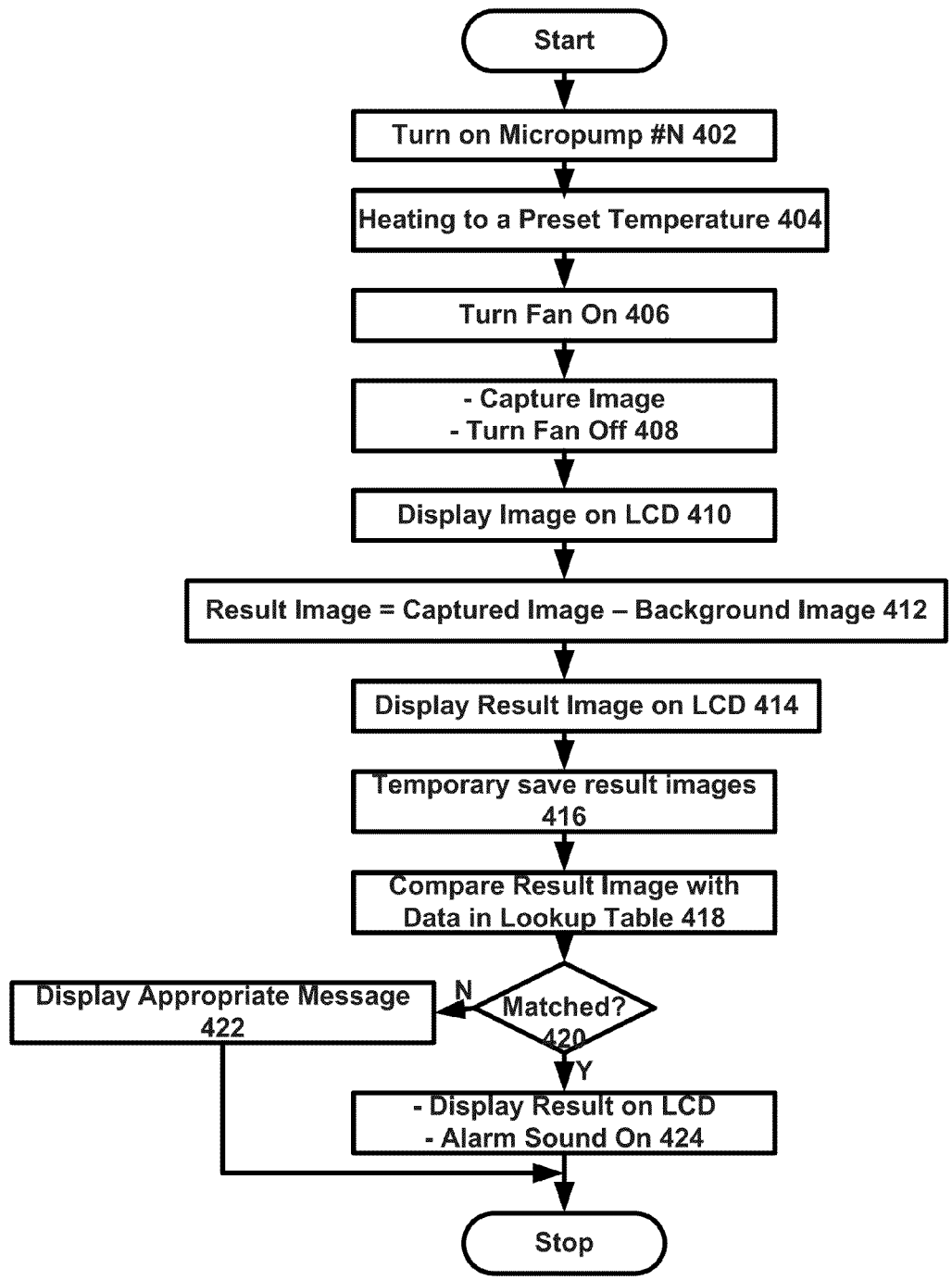
FIG. 8 shows an exemplary image analysis process executed by the processor of FIG. 5 to detect chemical agents automatically.

FIG. 8 shows an exemplary image analysis process executed by the processor 200 to detect chemical agents automatically. To start the analysis process, the system turns the micro-pump(s) N (i.e., N=1, 2, 3 . . . or a combination thereof) to disperse the chemical solution into the Swiped Sample. The pumping rate is set to 2 Hz. After dispersing chemical solution, the system starts heating the sample to excite the chemical reactions. A current of about 1 Ampere is required to heat up the filament. When the temperature of the sample reaches to a predefined value, the system turns the heater off, the LED and the fan on. In one embodiment, before commanding the CMOS image sensor to capture an image, the system waits for the chemical reaction under optimized: time, temperature, volume dispensed, and vapor to complete for around 1 ms. The captured image is then displayed on the LCD. The system creates a result image by subtracting the captured image from the background one. Then the result image is compared with the color patterns in the lookup table stored in the memory. If the results image matches some pattern, the result will be displayed and an audible alarm is given. Otherwise, an appropriate message is displayed on the LCD.

Due to the automated analysis, the system provides an objective indication of potential threats with more accurate results and more convenience.

The invention may be implemented in hardware, firmware or software, or a combination of the three. Preferably the invention is implemented in a computer program executed on a programmable computer having a processor, a data storage system, volatile and non-volatile memory and/or storage elements, at least one input device and at least one output device.

By way of example, a block diagram of a computer to support the system is discussed next. The computer preferably includes a processor, random access memory (RAM), a program memory (preferably a writable read-only memory (ROM) such as a flash ROM) and an input/output (I/O) controller coupled by a CPU bus. The computer may optionally include a hard drive controller which is coupled to a hard disk and CPU bus. Hard disk may be used for storing application programs, such as the present invention, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link. Optionally, a display, a keyboard and a pointing device (mouse) may also be connected to I/O bus. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

Each computer program is tangibly stored in a machine-readable, removable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A method to analyze a disposable test swipe, comprising:
   uniformly heating the disposable test swipe to a predetermined test area on the test swipe in a test chamber;
   exposing the test swipe through predetermined timed temperature sequences;
   dispensing chemicals in timed sequences onto the predetermined test area throughout a predetermined temperature profile and time sequence; and
   capturing a sequence of colors evolving specific to each analyte on the test area of the disposable swipe for differentiating, detecting, or identifying specifically one of a plurality explosives by taking a series of images, at specific heat and times in the sequence of chemical reactions on the test area of the swipe for analysis.

2. The method of claim 1, comprising performing an analysis of the reaction images collected throughout a test run in real-time.

3. The method of claim 1, comprising controlling each pump to dispense one or more chemical solutions in a predetermined sequence.

4. The method of claim 1, comprising heating the test area on the swipe to one or more predetermined temperatures and hold times using an automatic ramped heating feedback control.

5. The method of claim 1, comprising:
   providing a camera and an optics system with anti-fog protection;
   displaying a camera output in real-time; and
   storing and viewing images with a JPEG encoder and decoder.

* * * * *